(12) United States Patent
Hull et al.

(10) Patent No.: US 6,546,076 B1
(45) Date of Patent: Apr. 8, 2003

(54) DIGITAL HIGH RESOLUTION X-RAY IMAGING UTILIZING AN IMAGING SENSOR

(75) Inventors: Richard Hull, Calmar (CA); Eugene Curatu, Oviedo, FL (US); Jack Plummer, Temecula, CA (US)

(73) Assignee: Wuestec Medical, Inc., Mobile, AL (US)

( * ) Notice: Subject to any disclaimer, the term of this patent is extended or adjusted under 35 U.S.C. 154(b) by 0 days.

(21) Appl. No.: 09/532,339

(22) Filed: Mar. 21, 2000

(51) Int. Cl.[7] ................................. H05G 1/64
(52) U.S. Cl. .................... 378/98.3; 378/98.8; 359/821
(58) Field of Search ............................. 378/988, 98.3, 378/44; 359/821

(56) References Cited

U.S. PATENT DOCUMENTS

| | | | |
|---|---|---|---|
| 4,736,397 A | 4/1988 | Velasquez | 378/98.3 |
| 5,235,191 A * | 8/1993 | Miller | 378/62 |
| 5,367,405 A | 11/1994 | Sado | 359/649 |
| 5,452,337 A | 9/1995 | Endo et al. | 378/4 |
| 5,617,463 A | 4/1997 | Beierlein | 378/98.3 |
| 5,790,629 A | 8/1998 | Svensson et al. | 378/98.3 |
| 5,864,146 A * | 1/1999 | Karellas | 378/169 |

* cited by examiner

*Primary Examiner*—Drew A. Dunn
(74) *Attorney, Agent, or Firm*—Fulbright & Jaworski L.L.P.

(57) ABSTRACT

A system and method for high resolution digital x-ray imaging which utilizes a single imaging sensor is disclosed. In the preferred embodiment, the system utilizes a single imaging sensor and includes one or more redirecting elements to redirect a predetermined portion of light from an imaging screen onto the imaging sensor.

26 Claims, 2 Drawing Sheets

DIGITAL HIGH RESOLUTION X-RAY IMAGING UTILIZING AN IMAGING SENSOR

RELATED APPLICATIONS

The present application is related to commonly owned and co-pending U.S. patent application Ser. No. 09/449,173, entitled "AUTOMATIC EXPOSURE INITIATION IN A DIGITAL CCD CAMERA X-RAY SYSTEM", the disclosure of which is incorporated herein by reference. The present application is also related to commonly owned and copending U.S. patent application Ser. No. 09/449,172, entitled "DIGITAL HIGH RESOLUTION X-RAY IMAGING", the disclosure of which is incorporated herein by reference. The present application is also related to commonly owned and co-pending U.S. patent application Ser. No. 09/449,174, entitled "OPTICAL DISTORTION CORRECTION IN DIGITAL IMAGING", the disclosure of which is incorporated herein by reference. The present application is also related to commonly owned and co-pending U.S. patent application Ser. No. 09/449,046, entitled "IMAGE REDIRECTION AND OPTICAL PATH FOLDING", the disclosure of which is incorporated herein by reference.

TECHNICAL FIELD

The present invention relates to high resolution digital imaging and in particular to a digital x-ray imaging system and method utilizing a single digital camera.

BACKGROUND

In conventional x-ray imaging a photographic film is exposed to visible light produced by a fluorescent imaging screen in response to x-ray energy which has passed through an object, in order to capture the image of the object being x-rayed. The x-rays are passed through the object and impinge on the fluorescent imaging screen, such as a phosphor imaging screen. The phosphor imaging screen converts some of the radiation into a selected spectral component (typically visible light). The exposure of the photographic film to the spectral component from the phosphor imaging screen produces the image of the object on the photographic film.

Recent advances in x-ray imaging however have resulted in filmless x-ray methods and apparatus. Such a system is disclosed in U.S. Pat. No. 5,309,496, entitled "FILMLESS X-RAY APPARATUS AND METHOD OF USING THE SAME", issued to Winsor, which is hereby incorporated herein by reference. In the preferred embodiment of Winsor, a video camera and a frame grabber are used to provide still x-ray images.

However, in x-ray imaging it is desirable to get very high resolution images so that a health care provider could accurately diagnose a patient. The use of photographic films as used in conventional x-ray imaging systems provides a high degree of resolution desirable in x-ray radiography. However, the video camera and frame grabber of Winsor may not provide the desired high degree of resolution because in the preferred embodiment video camera and frame grabber implementation of Winsor, an image in analog format is filmed by the video camera and a frame grabber used to capture one or more frames. The captured frames may then be digitized. Because of the capture of the image in analog format and the subsequent conversion of the image from analog format to digital format, the desired degree of resolution may not be obtained. Also, as the video tube of the video camera has a fixed life span, it deteriorates over time and accordingly the quality of the image deteriorates over time, which may be evidenced for example by a decrease in the contrast of the image.

Furthermore, in any imaging system, because of the curvature of the lens (or lens assembly), more light passes through the center of the lens than through the edges. Therefore, the intensity of the pixels in the center is greater than the intensity of the pixels at the edges. Because of limitations of the video camera and frame grabber of the preferred embodiment of Winsor, the pixel contrast and/or intensities cannot be modified on an individual basis and therefore, in the final x-ray image the pixels at the center are brighter than those at the edges.

An alternative structure for capturing images is the use of multiple CCD (charge coupled device) cameras. The use of multiple digital cameras is known in other fields. In such applications, different cameras are used to capture different portions of the entire image thereby providing multiple images, which are later merged together in order to create a single image. However, in such applications, a known reference point is added to the original image itself. The different images are merged together using the known reference point. By utilizing the known reference point in the merging process, the combining of the images may be accomplished more efficiently. This procedure, however, adds unwanted artifacts (the reference point itself) to the image. The presence of artifacts in the combined image would be specially undesirable in an x-ray imaging system because of the degree of accuracy preferred in rendering a correct diagnosis of the patient based on the x-rays.

Moreover, in systems that use multiple CCD cameras, it is desirable that the multiple cameras be properly aligned with the object or imaging screen to be photographed. Because of the number of cameras involved in a multiple camera system this process may be quite cumbersome and time consuming. Additionally, proper alignment of the lens, mirror or prism with respect to the object plane, is also desirable. The process of alignment and calibration is very cumbersome and time consuming.

Furthermore, it is desirable to keep the brightness of the different portions of the image consistent especially with varying degrees of light intensity. Accordingly, there are several disadvantages of using multiple digital cameras, although the use of such multiple digital cameras has its associated advantages, such as higher resolution of the image.

Therefore, there is a need in the art for a system and method for rendering high resolution digital x-ray images of an object without the use of multiple cameras.

SUMMARY OF THE INVENTION

These and other objects, features and technical advantages are achieved by an x-ray imaging system and method which utilizes a single imaging sensor to acquire an image from an imaging screen.

In a preferred embodiment, the x-ray imaging system comprises a single imaging sensor, such as a digital CCD camera. The digital camera preferably acquires the image from an imaging screen, such as for example, a fluorescent phosphor screen used in x-ray imaging. The digital camera is positioned so that the field of view of the digital camera substantially covers the imaging screen. Light from the imaging screen falls on a redirecting element which redirects the light from the imaging screen onto a lens assembly of the imaging sensor. The elements of the lens assembly focus the image of the object onto a CCD chip which is preferably part of the imaging sensor.

In the preferred embodiment, the imaging apparatus also includes a host processor based system comprising a camera interface for receiving and processing the image from the camera. Such a host processor based system may be for example, a general purpose computer. A preferred embodiment host processor based system is described in the above referenced U.S. patent application entitled "DIGITAL HIGH RESOLUTION X-RAY IMAGING", which is hereby incorporated herein by reference.

Accordingly, it is a technical advantage of a preferred embodiment of the present invention to provide a high resolution digital x-ray imaging system.

It is another technical advantage of a preferred embodiment of the present invention to provide a seamless x-ray image.

It is still another technical advantage of a preferred embodiment of the present invention to provide high resolution x-ray images without any undesirable image artifacts.

It is still another technical advantage of a preferred embodiment of the present invention that the electronics components associated with an imaging sensor are not subjected to x-ray radiation as they are not directly in the path of the x-ray.

It is still another technical advantage of a preferred embodiment of the present invention to reduce the cost of digital x-ray imaging due to reduction in the number of cameras used.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWING

For a more complete understanding of the present invention, and the advantages thereof, reference is now made to the following descriptions taken in conjunction with the accompanying drawing, in which.

DETAILED DESCRIPTION

Figure 1:
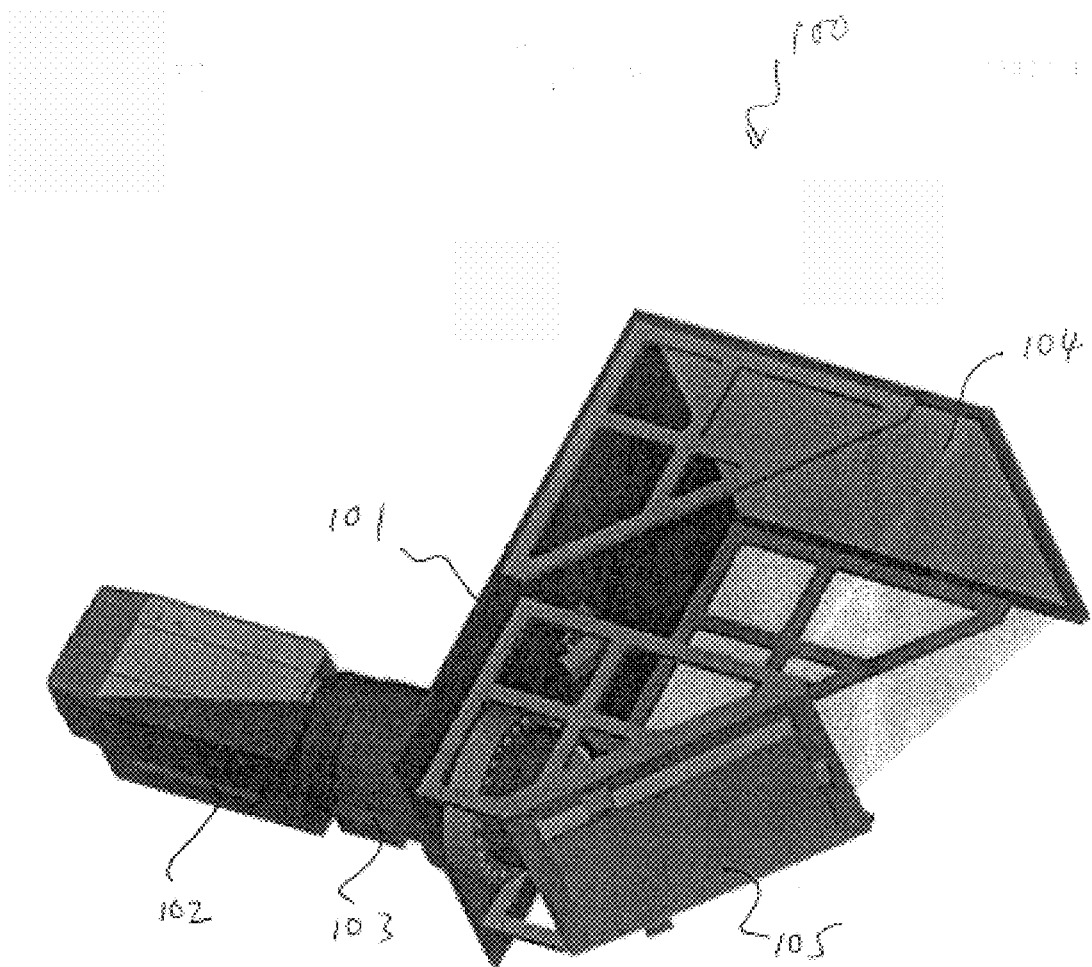
FIG. 1 shows a cutaway view of an imaging system of a preferred embodiment of the present invention.

FIG. 1 shows a cutaway view of an imaging system 100 of a preferred embodiment of the present invention. As shown in FIG. 1, imaging system 100 comprises a housing 101 and a single imaging sensor 102 aligned in an orientation so as to capture an image from an imaging screen 104. Imaging system 100 also comprises a redirecting element 105 to redirect light from the imaging screen 104 on to the imaging sensor 102.

Housing 101 is preferably a rigid, light tight, box made of aluminum. One side of housing 101 is preferably made up of a radio-transparent plastic and a phosphor imaging screen 104. Imaging screen 104 is preferably provided along the top portion of the camera housing 101. The housing provides a means for fixing the position of the imaging screen 104 in relation to the imaging sensor 102. The particular configuration of the housing and the camera as shown in FIG. 1 is not relevant to the invention covered by the present application.

In the preferred embodiment, imaging screen 104 is a fluorescent phosphor screen used in X-ray imaging. Also, in the preferred embodiment the imaging sensor 102 comprises a digital camera, preferably a digital CCD camera. The CCD camera of the preferred embodiment comprises, a photosensitive plate, such as a CCD chip (shown in FIG. 2) and a lens assembly (or lens) 103.

As shown in FIG. 1, the redirecting element 105 is preferably a front-surfaced mirror, preferably trapezoidal in shape. The front surface reflects the visible light while passing x-ray radiation. The back of the mirror is preferably coated with a substance, such as lead, to absorb x-ray radiation. The redirecting element 105 is preferably positioned at a 45 degree angle to the plane of the object or the imaging screen. The trapezoidal shape of mirror 105 allows the mirror to encompass the entire field of view of its associated CCD camera 102. The camera and its associated electronics components are used to acquire the image from the imaging screen. Moreover, the trapezoidal shape of the mirror allows the captured image to be rectangular in shape, thereby preventing a keystoning effect which would produce a trapezoidal image. Another advantage of using a trapezoidal mirror instead of a rectangular mirror is that the weight of a trapezoidal mirror is less than the corresponding rectangular mirror.

Visible light from imaging screen 104 is redirected by the redirecting element 105. The redirected light from redirecting element 105 falls onto lens 103 and is captured by imaging sensor 102. The image folding path is shown in greater detail in FIG. 2.

Figure 2:
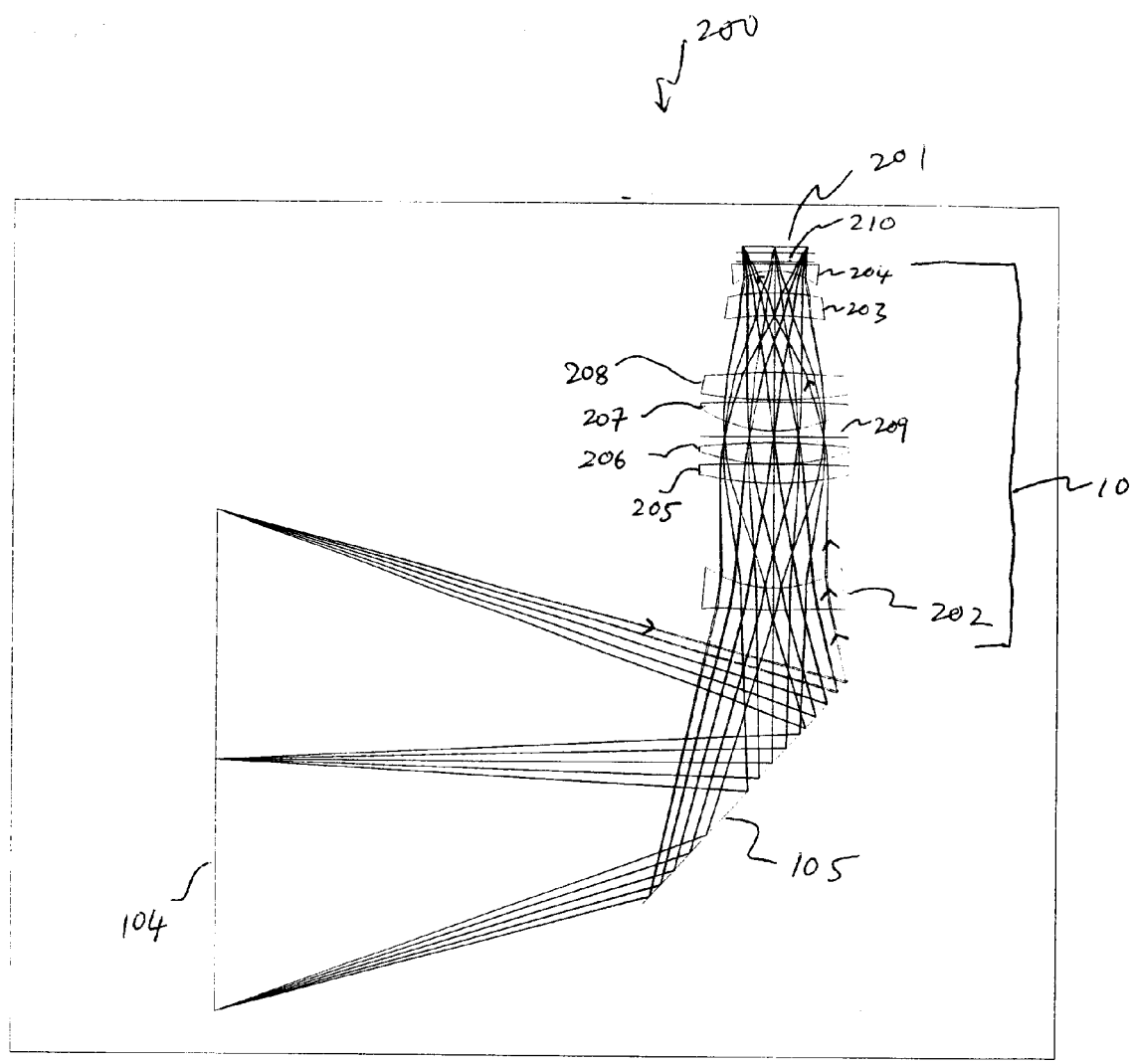
FIG. 2 shows a schematic representation of an image folding path using the preferred embodiment system for high resolution digital imaging.

FIG. 2 shows a schematic representation of an image folding path using the preferred embodiment system for high resolution digital imaging. In the preferred embodiment, imaging screen 104 is exposed to light (including radiation) in order to capture the image of the object (not shown) being x-rayed. The x-rays are passed through the object and impinge on the imaging screen 104. The imaging screen converts a substantial portion (preferably approximately 80%) of the radiation into a selected spectral component (typically visible light). The exposure of the CCD chip 201 (which in the preferred embodiment is part of imaging sensor 102) to the spectral component from the imaging screen produces the image of the object on the CCD chip.

As the imaging screen 104 does not convert all the x-rays, there is some residual portion of the x-rays left in the light coming from the imaging screen. When imaging with a sensor which may be exposed to high energy x-ray radiation, there is the potential for the imaging sensor and associated electronics to be damaged by such x-ray radiation. Moreover, the radiation energy in the light may produce undesirable image artifacts in the captured image. The imaging system shown in FIGS. 1 and 2 solves this problem in part by redirecting the light from the imaging screen 104 in such a manner as to place the imaging sensor 102 and its associated electronics out of the path of the x-ray radiation. In the system shown in FIGS. 1 and 2, the light from the imaging screen is redirected by a redirecting element before being provided to the imaging sensor. This solves in part the problems associated with image artifacts and prevents damage to the imaging sensor that may be caused due to exposure to high energy radiation.

Lens assembly 103 is preferably a sub f-1.0 relay lens. Based on an energy budget calculation, it is desirable that the f-number be low in order to provide sufficient number of photons when the phosphor screen is at a low energy. As shown in FIG. 2, in the preferred embodiment, lens assembly 103 comprises a plurality of lens elements. Preferably, lens assembly 103 comprises seven elements 202, 203, 204, 205, 206, 207 and 208. The first part (the part closer to the redirecting element 105) of the lens assembly 103 is preferably divergent and provides a wide field of view. The second (or central) part of the lens assembly 103 preferably provides the overall positive power of the lens. The third part (the part closer to the CCD chip 201) preferably reduces the aberration in the light provided to the CCD chip.

Preferably four of these seven elements are made of plastic and the rest are made of glass. In the preferred embodiment the plastic used is a polycarbonate plastic. In the embodiment of FIG. 2, elements 202, 203 and 204 are made of glass and elements 205, 206, 207 and 208 are made of plastic. The plastic elements are used in the preferred embodiment because they are less expensive than the glass elements. Moreover, plastic elements weigh less than glass elements thereby reducing the overall weight of the imaging system of the preferred embodiment. Accordingly, if desired, in alternative embodiments all the lens elements may be made of a plastic material. Also in the preferred embodiment, each plastic element comprises at least one aspheric surface. The high speed and the wide field of view requirements make the use of aspheric surfaces of particular interest for this application. The aspheric surfaces include multiple radius of curvatures as opposed to spherical surfaces which have only one radius of curvature. In order to limit the thermal drift of lens parameters, the glass elements comprise a substantial portion of the lens power.

A f-stop aperture 209 is provided preferably in between lens element 206 and 207. The f-stop aperture location allows controlling of monochromatic aberrations as well as minimizing of the lens element dimensions. The smaller the hole of the f-stop aperture 209, the better the picture. However, the use of the f-stop aperture results in loss of light. The loss in light can be remedied by providing a higher intensity light. In the preferred embodiment, the f-stop is mechanically controlled for electromechanical selection of the size of the f-stop, especially the size of the aperture in the f-stop. The size of the f-stop may be selected to provide a desired balance between contrast and illumination. Furthermore, more than one fstop aperture may be used, if desired. Also, if desired, an iris may be used in place of or in addition to the f-stop.

An optical field flattener 210 is preferably placed close to the CCD chip between lens element 204 and CCD chip 201 to correct the field curvature. Since the field flattener is placed in close proximity to the plane of the CCD, dirt, scratches, and other imperfections could be imaged onto the final image. Therefore, it is desirable that the optical field flattener be made of a material having a low bubble glass. The low bubble glass is preferably a B0 or D1 glass.

The lens of the preferred embodiment has a large aperture which is desirable to ensure a bright image. In the preferred embodiment, the aperture size is f-0.8. In alternative embodiments, the aperture size can be in the range of f-0.8 and f-1.0. Even though the lens covers only a limited spectral band, the chromatic correction has been taken into consideration. Despite the relatively low resolution of an X-ray image, a high Modulation Transfer Function (MTF) is desirable to maintain the quality of the image at high resolution. The MTF measures the ability of a lens assembly (or lens) to resolve fine details in an image. The MTF measures the percentage of light that goes through the aperture. A wide aperture has an MTF of approximately 100% which means that the dark areas of the imaging screen appear dark on the image and the white areas of the imaging screen appear white on the image. If the slots are narrower, the white areas of the imaging screen appear smeared or merge with the other points on the screen. This makes it difficult to read these points. The MTF of the preferred embodiment imaging system of the present invention is at least 30% and preferably approximately 80%. The MTF value of the lens assembly of the preferred embodiment varies from approximately 92% at the center to approximately 30% at the edges.

As shown in FIG. 2, in the preferred embodiment, light from imaging screen 104 falls on the redirecting element 105. The redirecting element 105 redirects the light from imaging screen 104 onto lens assembly 103 of the imaging sensor. The plurality of elements of lens assembly 103 focus the image of the object onto CCD chip 201 of imaging sensor 102. CCD chip 201 is capable of capturing the image of the imaging screen.

The CCD camera of the preferred embodiment is preferably connected to a host processor based system by a data transfer mechanism. The image so captured is preferably fed to the host processor based system. The host processor based system preferably processes the image via a dark frame, flat field and/or distortion correction software to provide a corrected image as discussed in detail.

The host processor based system is preferably a general purpose computer, such as a Personal Computer (PC) of known and conventional configuration. The camera is connected to a suitable camera interface card which is associated with the host system. The camera interface card is preferably of the same type as used by the camera manufacturer.

Software running on the host computer facilitates interfacing of the host computer with more than one camera, if desired. Thus, the host computer is capable of receiving image information from multiple cameras. Depending on the specific commands transmitted to the cameras, the technique of transmitting data may follow either a sequential or parallel order, i.e. data may be sent between the cameras and the host computer either in series or in parallel. The parallel method utilizes the timing pauses of the communication protocol to speed up operation by transmitting data to other cameras during a pause associated with a particular camera. When the host computer is capable of transmitting data at a higher rate than the camera interface, the parallel method may be used. Accordingly, the host computer may communicate with one or more camera(s) during protocol delays with a given camera. The host computer is capable of performing many more operations in the same amount of time as the cameras are capable. An automatic exposure initiator used to trigger the capture of images is disclosed in the above mentioned U.S. patent application, entitled "Methods and Apparatus for Automatic Exposure Initiation in a Digital CCD X-Ray System", the disclosure of which is hereby incorporated herein by reference. Another method of capturing an image would be to activate the imaging sensor as soon as the x-ray source is initiated.

Optical defects, if any, in the captured image may be corrected in software as disclosed in the above mentioned U.S. patent application, entitled "Optical Distortion Correction in Digital Imaging", the disclosure of which is hereby incorporated herein by reference.

Because of the differences in the sensitivity and noise factor between pixels within a CCD chip, the image captured may have a disparity in brightness between pixels. Each pixel in a CCD image may be normalized by using dark frame and flat field images. Dark frame images are acquired in total darkness; the intensity values obtained indicate noise due to heat and electronics. Flat field images are acquired using an integrating sphere in which the light is substantially uniform. Differences between pixels in a flat field image indicate differences in operating characteristics of cells within the CCD chip. Each pixel within a digital image is corrected on a pixel-by-pixel basis using the following formula:

$$I_{improved} = (I_{original} - I_{dark}) / (I_{flat} - I_{dark}),$$

where:

$I_{improved}$ is the improved image;

$I_{original}$ is the original image;

$I_{flat}$ is the flat field (image with substantially the same amount of light on each pixel); and $I_{dark}$ is the dark frame (image with no light).

Thus, the variations may be removed by the above process. After dark frame and flat fielding, each pixel has a normalized value between 0 and 1, wherein the brightest pixels have a value of 1. The pixels are then scaled by a scaling factor. For example, when using 8 bit pixels, the normalized pixel values are scaled by $2^8$.

In a multi-camera system utilizing, say four cameras, each camera is focused on the center of portion of imaging screen (typically a quadrant) which is being imaged by the particular camera. None of the cameras in a four camera system are typically focused on the center of the imaging screen. An advantage of the single camera system of the preferred embodiment is that the camera is focused preferably at the center of the imaging screen to be captured. Focusing the camera at the center of the imaging screen provides a better quality picture than focusing it on other portions of the screen.

Although high resolution digital CCD cameras are expensive, the availability of large array CCDs, for example CCDs with 4 k×4 k pixels provides the high level of resolution desirable for diagnostic x-ray imaging without the use of multiple imaging sensors. Accordingly, the preferred embodiment system and method of the present invention is capable of providing digital high resolution x-ray imaging for large imaging screens. For example, the preferred embodiment system and method is capable of providing a high resolution digital x-ray image of screen sizes, such as 14 inches by 17 inches, 17 inches by 17 inches and other similar screen sizes.

Although a single mirror is used in the preferred embodiment to redirect light from the imaging screen to the imaging sensor, the invention is not so limited. In alternative embodiments, multiple redirecting elements may be used to redirect the light from the imaging screen multiple times before being provided to the imaging sensor.

Moreover, although in the preferred embodiment a mirror is used as a redirecting element, the invention is not so limited, and prisms may be used for redirection. For example, a prism comprising one reflecting surface may be used as the redirecting element discussed above, if desired. This is specially useful when the lens assembly is located outside the camera housing instead of inside the camera housing. Moreover, shaped mirrors (for example catadioptric lens) may be used if desired.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An x-ray apparatus for capturing an image from an imaging screen, comprising:

a source of x-rays disposed for directing x-rays through an object, wherein said object is positioned between said x-ray source and an imaging screen, and wherein said imaging screen is disposed at least partially in the path of said x-rays passing through said object;

a digital imaging subsystem for capturing an image from at least a portion of said imaging screen, wherein said imaging subsystem comprises a redirecting element for redirecting visible light from said portion of said imaging screen onto an imaging sensor, wherein said portion of said imaging screen is positioned between said x-ray source and said redirecting element, wherein said imaging sensor comprises a lens assembly to focus said image received from said portion of said imaging screen; and a processor based system, wherein said processor based system is communicatively connected to said digital imaging subsystem, wherein said captured image is provided to said processor based system, wherein said processor based system converts a pixel intensity value of each pixel of said captured image into an improved pixel intensity value, wherein said improved pixel intensity value for each pixel is given by the equation:

$$I_{improved} = (I_{original} - I_{dark}) / (I_{flat} - I_{dark}),$$

wherein $I_{improved}$ is the improved pixel intensity value;

$I_{original}$ is the original pixel intensity value;

$I_{flat}$ is a flat field pixel intensity value; and $I_{dark}$ is a dark frame pixel intensity value.

2. The x-ray apparatus of claim 1, wherein said imaging screen is a fluorescent phosphor screen.

3. The x-ray apparatus of claim 1, wherein said redirecting element is positioned at a 45 degree angle to a plane of said imaging screen, and wherein said redirecting element is adapted to encompass a field of view of said imaging sensor.

4. The x-ray apparatus of claim 1, wherein a shape of said redirecting element is selected to encompass the field of view of said imaging sensor.

5. The x-ray apparatus of claim 1, wherein said redirecting element is a mirror adapted to redirect light from said portion of said screen onto said imaging sensor.

6. The x-ray apparatus of claim 5, wherein said redirecting element redirects only a predetermined portion of said light received from said portion of said screen onto said imaging sensor.

7. The x-ray apparatus of claim 1, wherein said redirecting element is a mirror adapted to absorb x-ray radiation.

8. The x-ray apparatus of claim 1, wherein said imaging sensor comprises:

a photosensitive plate for capturing said image.

9. The x-ray apparatus of claim 1, wherein said lens assembly is a sub f-1.0 relay lens.

10. The x-ray apparatus of claim 1, wherein said lens assembly comprises a plurality of lens elements.

11. The x-ray apparatus of claim 10, wherein a selected plurality of said plurality of lens elements are made of a plastic material and the remaining lens elements are made of glass.

12. The x-ray apparatus of claim 8, wherein said lens assembly comprises seven lens elements, wherein three of said seven lens elements are made of glass and four of said seven lens elements are made of a plastic material.

13. The x-ray apparatus of claim 12, wherein said plastic material is a polycarbonate.

14. The x-ray apparatus of claim 8, wherein at least one element of said lens assembly comprises at least one aspheric surface.

15. The x-ray apparatus of claim 14, wherein at least another element of said lens assembly comprises at least one spherical surface.

16. The x-ray apparatus of claim 11, wherein each of said plurality of plastic lens elements includes at least one aspheric surface.

17. The x-ray apparatus of claim 11, wherein each of said plurality of glass lens elements includes at least one spherical surface.

18. The x-ray apparatus of claim 10, wherein said lens assembly further comprises:

an f-stop aperture for controlling an amount of monochromatic aberration in said light provided to said imaging sensor, wherein said f-stop aperture is located between two lens elements of said plurality of lens elements of said lens assembly.

19. The x-ray apparatus of claim 18, further comprising:

an optical field flattener to correct a field curvature, wherein said optical field flattener is located between said lens assembly and said photosensitive plate.

20. The x-ray apparatus of claim 8, wherein a Modulation Transfer Function (MTF) of said lens assembly is at least 30%.

21. The x-ray apparatus of claim 8, wherein said photosensitive plate is a Charge Coupled Device (CCD) chip and said imaging sensor is a CCD camera.

22. The x-ray apparatus of claim 1, further comprising:

means for fixing the position of said imaging screen in relation to said imaging sensor.

23. The x-ray apparatus of claim 1, wherein said imaging sensor is not directly in the path of said x-rays from said x-ray source.

24. The x-ray apparatus of claim 1, wherein said flat field pixel intensity value is the pixel intensity value for an image with substantially the same amount of light on each pixel.

25. The x-ray apparatus of claim 1, wherein said dark frame pixel intensity value is the pixel intensity value for an image with no light.

26. The x-ray apparatus of claim 1, wherein said processor based system provides lens artifact correction to said captured image.

* * * * *